(12) United States Patent
Ledoux et al.

(10) Patent No.: US 8,068,582 B2
(45) Date of Patent: Nov. 29, 2011

(54) METHODS AND SYSTEMS FOR THE DIRECTING AND ENERGY FILTERING OF X-RAYS FOR NON-INTRUSIVE INSPECTION

(75) Inventors: Robert J. Ledoux, Harvard, MA (US); William Bertozzi, Lexington, MA (US); Stephen E. Korbly, Acton, MA (US)

(73) Assignee: Passport Systems, Inc., Billerica, MA (US)

( * ) Notice: Subject to any disclaimer, the term of this patent is extended or adjusted under 35 U.S.C. 154(b) by 380 days.

(21) Appl. No.: 12/035,795

(22) Filed: Feb. 22, 2008

(65) Prior Publication Data
US 2008/0219408 A1    Sep. 11, 2008

Related U.S. Application Data

(60) Provisional application No. 60/891,277, filed on Feb. 23, 2007.

(51) Int. Cl.
*G21K 1/06* (2006.01)
(52) U.S. Cl. .................. 378/84; 378/82; 378/85
(58) Field of Classification Search .................. 378/71, 378/53, 57, 62, 73, 82, 84, 85
See application file for complete search history.

(56) References Cited

U.S. PATENT DOCUMENTS

| | | | | |
|---|---|---|---|---|
| 4,429,411 A * | 1/1984 | Smither | ............ | 378/84 |
| 5,132,997 A * | 7/1992 | Kojima et al. | ............ | 378/85 |
| 5,245,648 A * | 9/1993 | Kinney et al. | ............ | 378/43 |
| 5,684,852 A | 11/1997 | Tomie et al. | | |
| 6,125,295 A * | 9/2000 | Cash et al. | ............ | 600/431 |
| 6,359,963 B1 * | 3/2002 | Cash | ............ | 378/65 |
| 6,366,801 B1 * | 4/2002 | Cash et al. | ............ | 600/431 |
| 6,389,100 B1 | 5/2002 | Verman et al. | | |
| 6,389,101 B1 * | 5/2002 | Levine et al. | ............ | 378/85 |
| 6,459,763 B1 * | 10/2002 | Koinuma et al. | ............ | 378/71 |
| 6,577,708 B2 * | 6/2003 | Chapman et al. | ............ | 378/82 |
| 6,782,073 B2 * | 8/2004 | Collins | ............ | 378/65 |
| 6,853,704 B2 * | 2/2005 | Collins et al. | ............ | 378/65 |
| 6,947,521 B2 * | 9/2005 | Wernick et al. | ............ | 378/70 |
| 6,968,035 B2 * | 11/2005 | Siochi | ............ | 378/65 |
| 7,206,375 B2 * | 4/2007 | Chen et al. | ............ | 378/51 |
| 7,231,015 B2 * | 6/2007 | Kumakhov | ............ | 378/65 |
| 7,742,564 B2 * | 6/2010 | Parham et al. | ............ | 378/71 |

OTHER PUBLICATIONS

International Search Report and Written Opinion for PCT/US2008/054712.
F. Frontera, et al., "Haxtel: a Laue lens telescope for deep exploration of the hard X-ray sky ($\geq 60$ keV)" Conference on "Focusing Telescopes in Nuclear Astrophysics" Bonifacio, Sep. 12-15, 2005.
Halloin, Hubert et al., "Basics and Laue lens theory and simulations or crystallography applied to high energy astrophysics . . . ," Gamma Wave—Bonifacio—Sep. 2005.
Caroli, Ezio et al., "A focal plane detector design for a wide-band Laue-lens telescope"; *Experimental Astronomy*, vol. 20, Issue 1-3, pp. 341-351, 2005.
P. von Ballmoos, et al., "Crystal Diffraction Telescopes for Nuclear Astrophysics", Proc. SPIE vol. 2806, pp. 372-385, 1996.
Smither, Robert K et al., "Crystal Diffraction Lens Telescope for Focusing Nuclear Gamma Rays," SPIE, vol. 2806, pp. 509-523, 1996.

* cited by examiner

*Primary Examiner* — Allen C. Ho
(74) *Attorney, Agent, or Firm* — Foley Hoag LLP

(57) ABSTRACT

Systems and methods are disclosed herein for lenses based on crystal X-ray diffraction and reflection to be used to direct and energy filter X-ray beams.

26 Claims, 7 Drawing Sheets

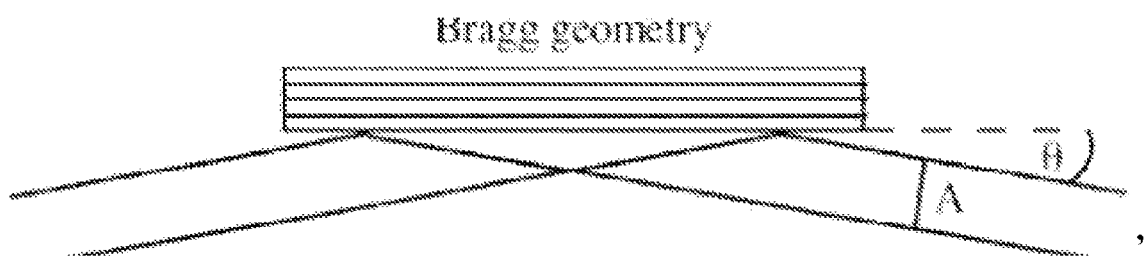
Figure 1A Bragg Geometry
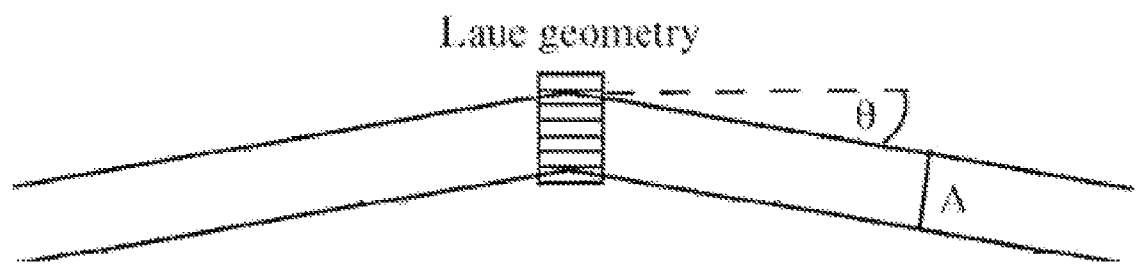
Figure 1B Laue Geometry

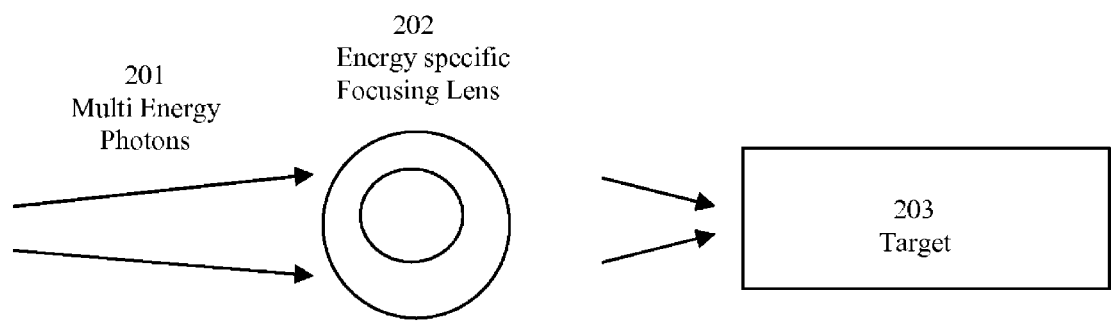
Figure 2: Use of crystal diffraction for focusing X-ray beam onto target

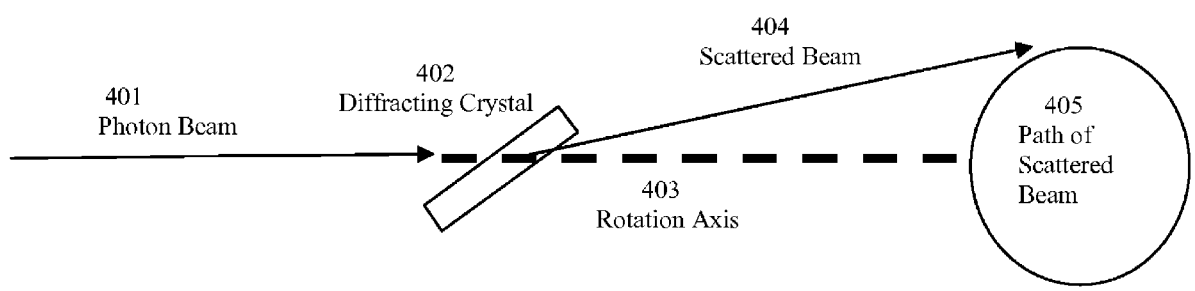
Figure 4. Use of crystal diffraction for scanning X-ray beam by rotating diffracting crystal

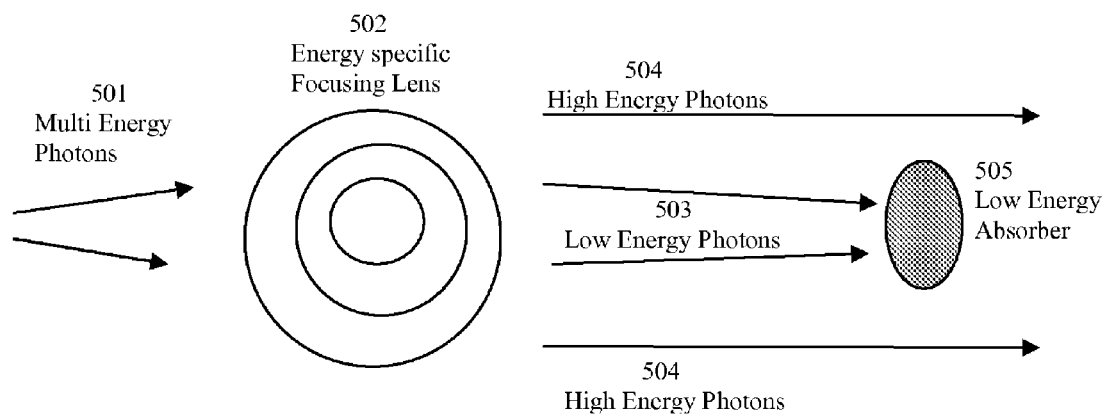
Figure 5A Use of crystal diffraction Laue lens for low energy filtering of continuous X-ray beam
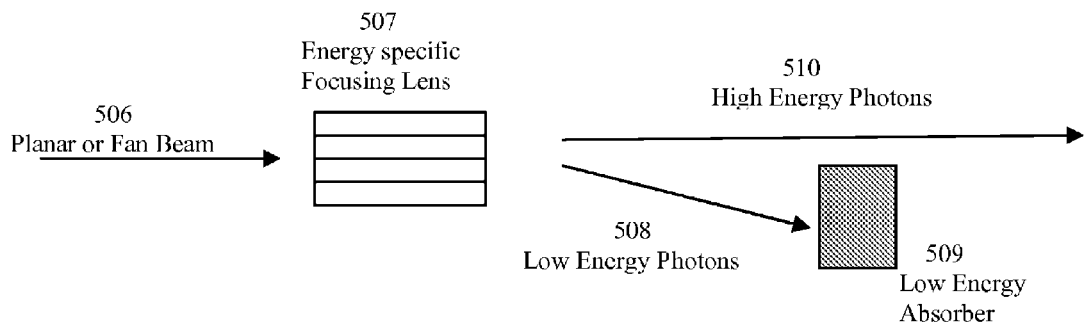
Figure 5B Use of crystal diffraction Laue lens for low energy filtering of continuous X-ray beam
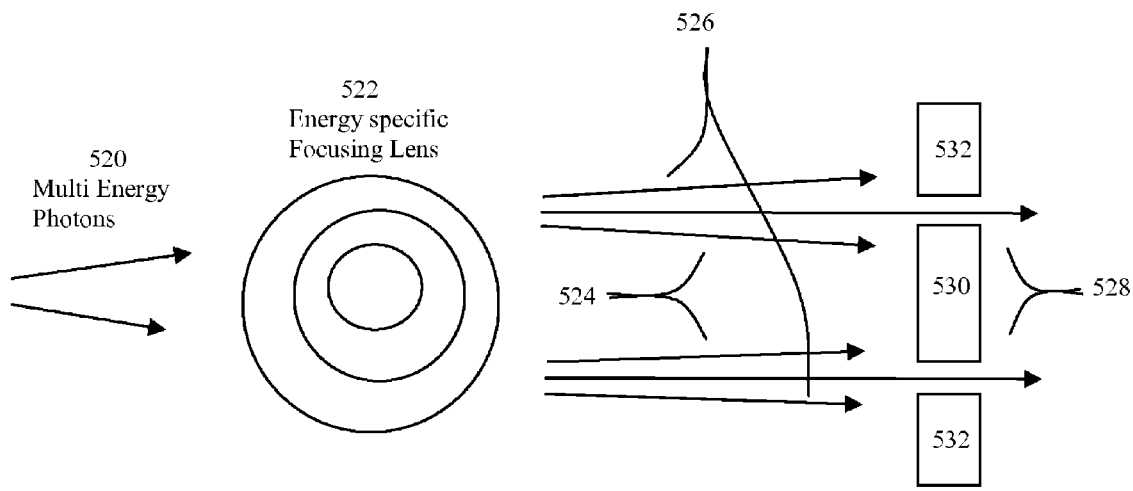
Figure 5C Use of crystal diffraction Laue lens for band pass filtering of continuous X-ray beam.

METHODS AND SYSTEMS FOR THE DIRECTING AND ENERGY FILTERING OF X-RAYS FOR NON-INTRUSIVE INSPECTION

PRIORITY CLAIM

This application claims priority to the following provisional patent application, the entirety of which is expressly incorporated herein by reference: U.S. Ser. No. 60/891,277 filed on Feb. 23, 2007, entitled "Methods And Systems For The Focusing, Directing and Energy Filtering of X-Rays For Non-Intrusive Inspection".

BACKGROUND

1. Field of the Invention

This patent application relates to systems and methods for the directing and energy filtering of X-ray beams via diffraction and reflection using crystals (including Laue and Bragg diffraction). Embodiments in the field of non-intrusive inspection technology are presented. The capability to direct and energy filter X-ray beams greatly expands existing and potential applications of X-ray based inspection technologies.

The term X-ray is used to denote penetrating electromagnetic radiation and it is interchangeable with other traditional characterizations that use terms such as photons, gamma-rays, etc. when referring to electromagnetic radiation in the X-ray energy range.

2. Background Information

There are a variety of inspection regimes where the use of a directed or energy filtered X-ray beam may be highly advantageous.

A common method for producing a high intensity X-ray source in the photon energy range greater than 100 keV is electron bremsstrahlung. However, the bremsstrahlung process produces a continuous energy distribution of photons that are only weakly forward peaked for electron beam energies under consideration in non-intrusive inspection. The ability to direct this beam to a distant point may increase the distance over which inspections are practical by overcoming the divergence of the X-ray beam between the location of its production and the target, and the ability to energy filter may be advantageous in reducing the energy distribution of the incident photons.

Similarly, X-rays scattered from a target will fall off in intensity as the distance between the target and a detector is increased. A method of capturing these X-rays and imaging them onto a small detector may be very advantageous, in particular when the detectors require high photon energy-resolution and are very expensive. The result may be an increase in the distance over which such a system can operate, an increase in detection signal, reduced noise, and reduced cost.

There are coherent, nearly mono-energetic sources of X-rays in which the divergence and size of the beam is very small. These coherent sources of X-rays may be very useful for remote inspection since their size even at tens of meters may only be a few centimeters in diameter. However, the ability to inspect large objects (of order a meter or greater) may require some method to scan the beam over the target. An efficient mechanism for directing such a coherent nearly mono-energetic X-ray beam would be desirable.

Techniques for implementing inspection regimes are discussed in U.S. Pat. No. 5,115,459, Explosives Detection Using Resonance Fluorescence of Bremsstrahlung Radiation, U.S. Pat. No. 5,420,905, Detection of Explosives and Other Materials Using Resonance Fluorescence, Resonance Absorption, and Other Electromagnetic Processes with Bremsstrahlung Radiation, U.S. Pat. No. 7,120,226, Adaptive Scanning Of Materials Using Nuclear Resonance Fluorescence Imaging, U.S. Patent Publication No. 2006/0188060A1, Use of Nearly Monochromatic and Tunable Photon Sources with Nuclear Resonance Fluorescence in Non-intrusive Inspection of Containers for Material Detection and Imaging, U.S. Patent Publication No. 2007/0145973A1, Methods And Systems For Active Non-Intrusive Inspection And Verification Of Cargo And Goods, and U.S. Pat. No. 7,286,638, Methods and Systems for Determining the Average Atomic Number and Mass of Materials, the contents of each of which are incorporated herein by reference.

SUMMARY OF THE INVENTION

We have developed systems and methods using crystal diffraction and reflection (including Laue and Bragg diffraction) for the directing and energy filtering of X-ray beams used in inspection systems. This may have the effect of increasing the efficiency and performance of inspection systems.

Examples of how the use of diffraction from crystals can direct or energy filter X-ray sources are summarized below.

The redirection of an X-ray beam can achieve an approximate focal point.

This reduces the $1/r^2$ dependence of the intensity of the X-rays on distance from a source or scatterer and increases the sensitivity of measurements particularly for remote target inspection.

The beam may be directed in a desired direction. For example, this can be used as a method for scanning the X-ray beam across a volume of interest.

Crystal diffraction and reflection can also be used to energy filter an X-ray beam with a wider energy distribution than desirable. This can be used to select a particular energy or energy range for inspection or to remove unwanted regions of the energy spectrum. This filtering may aid in reducing both the dose delivered to the inspection volume and the background from incident photons that do not contribute to the signal associated with the inspection method.

BRIEF DESCRIPTION OF THE DRAWINGS

The description below refers to the accompanying drawings, of which:

FIG. 1A illustrates the geometry of Bragg diffraction from a crystal.

FIG. 1B illustrates the geometry of Laue diffraction through a crystal.

FIG. 2 illustrates an exemplary procedure for the focusing of an X-ray beam onto a target.

FIG. 4 illustrates an exemplary procedure for the scanning of an X-ray beam in a circle by rotating the diffracting crystal about the beam axis.

FIG. 5A illustrates an exemplary procedure for the energy filtering of an X-ray beam.

FIG. 5B illustrates an exemplary procedure for the energy filtering of an X-ray beam.

FIG. 5C illustrates an exemplary procedure for the energy filtering of an X-ray beam.

DETAILED DESCRIPTION OF ILLUSTRATIVE EMBODIMENTS

Figure 3A:
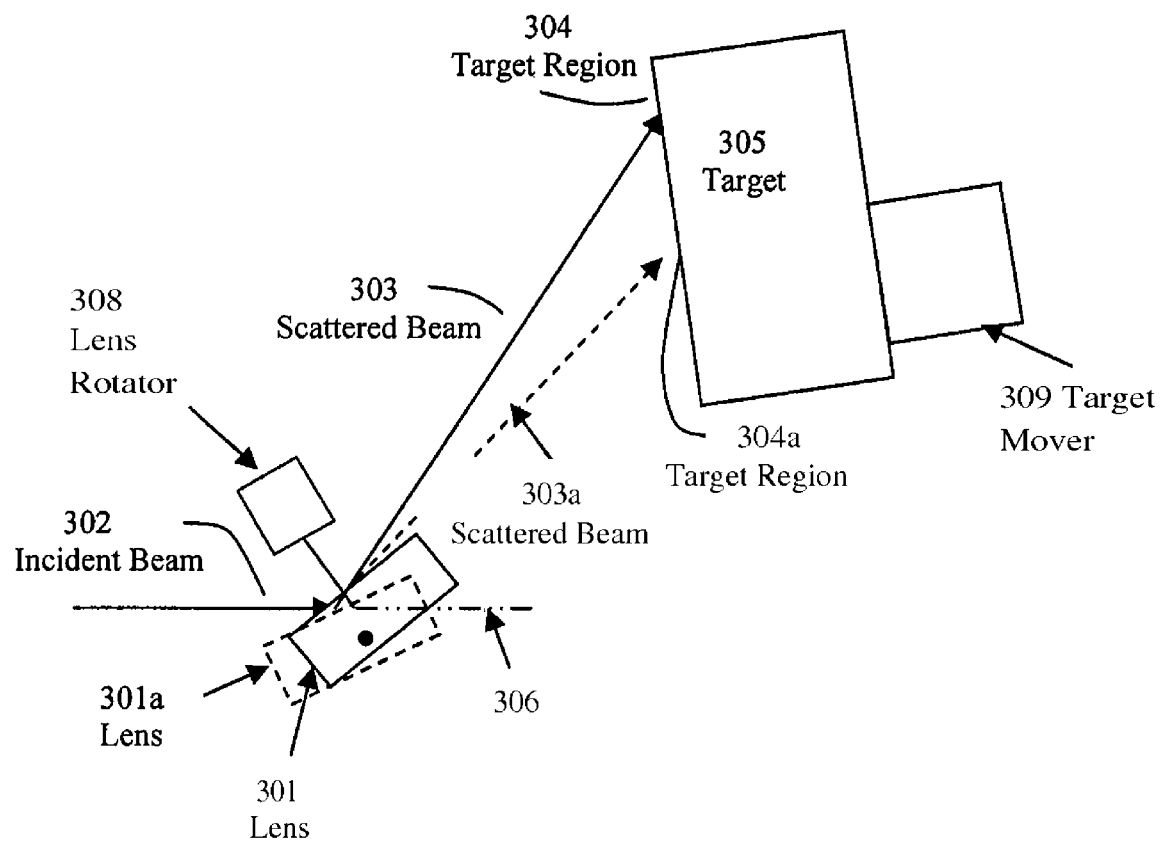
FIG. 3A illustrates an exemplary procedure for the directing of an X-ray beam by Bragg diffraction.

Unless otherwise specified, the illustrated embodiments can be understood as providing exemplary features of varying detail of certain embodiments, and therefore, unless otherwise specified, features, components, modules, and/or aspects of the illustrations can be otherwise combined, specified, interchanged, and/or rearranged without departing from the disclosed devices or methods. Additionally, the shapes and sizes of components are also exemplary, and unless otherwise specified, can be altered without affecting the disclosed devices or methods.

As shown in FIG. 1A, a crystal deflects photons of a specific energy incident on its surface at a particular angle via Bragg diffraction. The incident angle at which Bragg diffraction will occur, and the resulting angle of reflection, depend upon the crystal spacing and the incident photon energy according to principles that will be well understood by a person of skill in the art. In particular, $$2d \sin \theta = n\lambda,$$

where
d is the crystal spacing,
θ is the angle of incidence and reflection,
λ is the photon wavelength and
n is the order of the diffraction maximum.

Thus, for any given energy and crystal a specific angle of incidence determined by the above formula will lead to a reflected beam at an angle equal to the angle of incidence. (In FIG. 1A, A denotes the width of the incident or exiting beam.)

As shown in FIG. 1B, a crystal also deflects photons of specific energy that enter it through its surface at a particular angle via Laue diffraction. Again, the incident angle and the angle of outgoing deflection θ depend upon the crystal spacing and the incident photon energy according to principles that will be well understood by a person of skill in the art. As with Bragg diffraction, for each energy there will be maxima at certain transmitted angles, depending on the crystal spacing and orientation. Because crystals may have different spacings in different planes, the possible angles may vary with the crystal orientation. (In FIG. 1B, A again denotes the width of the incident or exiting beam.)

Directing of X-Ray Beams

An efficient mechanism for directing a coherent monoenergetic X-ray beam is to "steer" it using crystal diffraction, which may be either Laue or Bragg diffraction. The diffraction could be used to scan a beam across a target, or to increase detection sensitivity. A system of crystals could be used to irradiate a target or collect radiation from a target onto a detector. Embodiments of these principles are described hereinbelow, but we will first present an embodiment that takes advantage of Laue diffraction to enhance the available photon beam in a desired energy range by selectively directing photons in that energy range.

In FIG. 2, Laue diffraction is used to select X-rays in a particular energy range to be directed onto a target. A divergent beam of X-rays 201 with multiple energy components is incident on a crystal lens 202 composed of a plurality of crystal surfaces arranged in concentric circles.

For clarity the lens is shown rotated from its actual orientation in FIG. 2. (For example, as deployed the beam 201 is incident on the plane containing the crystal surfaces arranged in concentric circles, such that the central axis of the beam is substantially perpendicular to the plane containing the crystal lens.)

Through the appropriate choice of the crystal structures and their arrangement, according to principles known to those of skill in the art, this lens will select and direct a specific X-ray energy range with high efficiency. In particular, depending on the desired energy, and the crystal chosen, each crystal surface in a given concentric circle may be oriented at an appropriate angle such that photons of the desired energy range are incident on each crystal surface at a desired angle and are deflected in the desired direction. This energy-filtered beam can be used to interrogate a small region of a target 203. This technique increases the signal to noise ratio by focusing the beam on a smaller cross section while simultaneously reducing the background from other photons that do not contribute to the production of signal.

Crystals to be used for this application (and the other applications described herein) may be made from a variety of materials that will be known to a person of skill in the art, including in particular copper, carbon, silicon and germanium. In typical applications, the crystals will be on the order of 1 cm. thick and may be several cm. across. In general, crystals with small atomic spacing are effective in providing useful deflections at the energies of interest for target inspection using the approaches laid out in the patents and patent applications incorporated herein. In addition, materials with high electron density also are desirable, especially for higher energies. Gold and silver are excellent candidates as crystal materials.

A nearly monochromatic photon beam is often produced with a high degree of directionality due to the intrinsic processes used to produce the beam. Practical sources of nearly monochromatic photon beams are made possible by techniques such as laser backscattering from energetic electrons (among others). Such beams are well suited for example, for scanning of containers using Nuclear Resonance Fluorescence, in part because of the lower X-ray dose that is possible during an inspection of a container since the photon beam is concentrated in narrow regions of the energy spectrum. This is in contrast to a bremsstrahlung beam, which has photons at all energies below the end-point energy of the electron beam that produces it. One characteristic of the photon beams that result from laser backscattering is a photon beam that may be only a few centimeters in diameter at a distance of 30 meters (for one example) from the photon source. The direction of the photons is also a fixed parameter for each electron beam energy and laser photon energy. While these characteristics are very desirable in many situations, they represent a problem for scanning a container that may be many meters long and wide. Scanning the beam over the surface of a container generally is impractical if the directions of both the laser beam and electron beam are to be changed to accommodate each photon direction.

Crystal diffraction presents a method for such inspection because of its efficient deflection of a photon beam through an angle. For example, a crystal of a material such as copper (as one example) can deflect the photon beam through an angle such that a deflection of a meter is possible at a practical distance of tens of meters. By moving the crystal so as to change the angle of the crystalline planes relative to the beam axis, the photon deflection angle may be changed and thus the position of the beam on the target (container under inspection) may be moved. In addition, by suitably rotating the crystal so as to maintain the same incident angle, the direction of beam deflection may be changed. Thus, the photon beam may be scanned over the surface of a target that is many times the size of the beam spot. Crystals may have uniform structures and may be curved by thermal or mechanical means to provide focusing or defocusing as desired by the specific application.

A suitable crystal can be used to scan the photon beam across a region of interest by Bragg diffraction. In FIG. 3A, the specific direction of the scattered beam 303 is determined by the crystal spacing and the angle of crystal lens 301 that deflects the incident beam 302. (The incident angle should be chosen to represent a maximum of Bragg diffraction for the chosen crystal spacing and orientation and the desired photon energy.)

Mechanical motion of the lens 301 may be provided and controlled for positioning the lens 301 in continuous or stepwise motion. The motion may be rotary motion about an axis 306 to produce a range of possible lens positions shown for example as lens 301 and lens 301a. The lens may be rotated by a lens rotator 308. In particular, if the rotation is about an axis 306 that is along the incident beam direction 302, then as the crystal is rotated the incident angle will be constant, and Bragg scattering will continue at the maximum. Thus, depending on the controlled angular position of the lens 301 the scattered beam may follow the path indicated by scattered beam 303a or the path indicated by scattered beam 303, and/or may be scanned along a path between that of scattered beam 303 and scattered beam 303a and may be incident on target 305 at target region 304a or target region 304 (or at regions of the target 305 between target region 304 and target region 304a). (FIG. 3A only shows the beam deflection as a projection in the plane of the diagram, but there is also a component of deflection out of the diagram plane as the crystal lens 301, 301a rotates. See also the discussion hereinbelow of FIG. 4.)

Figure 3B:
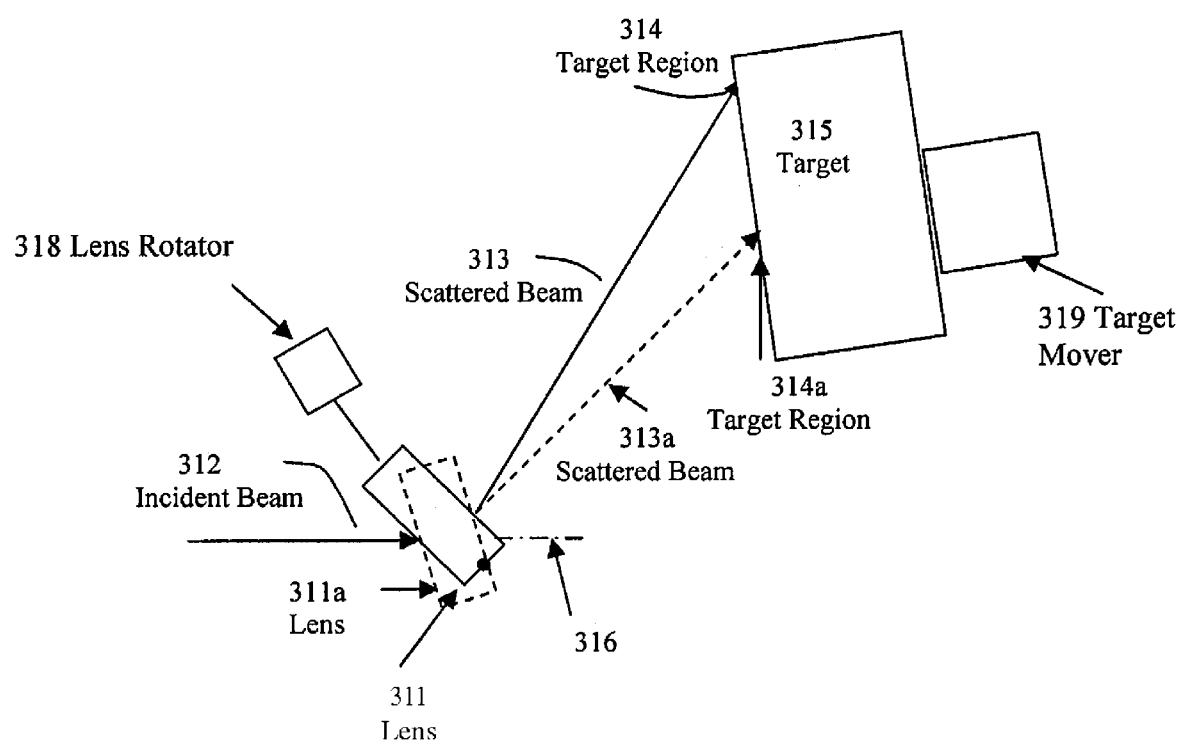
FIG. 3B illustrates an exemplary procedure for the directing of an X-ray beam by Laue diffraction.
Figure 3C:
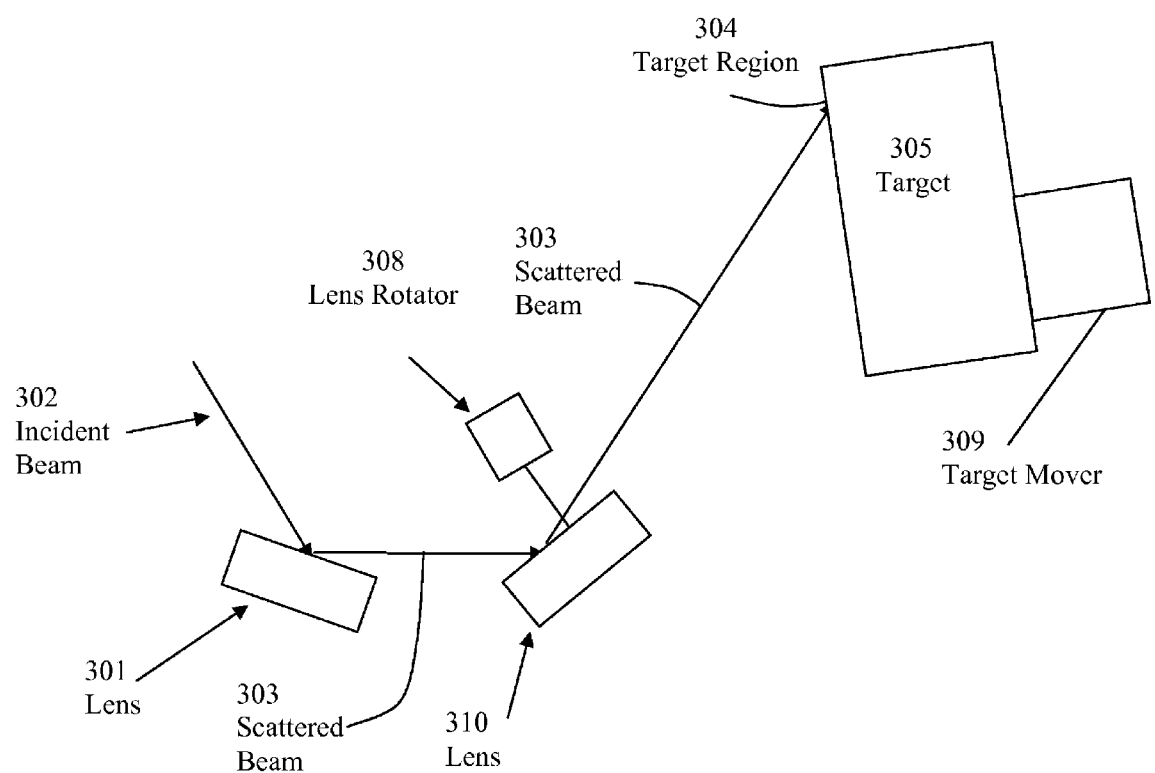
FIG. 3C illustrates an exemplary procedure for the directing of an X-ray beam by Bragg diffraction.

A series of lenses may be used, as illustrated in FIG. 3C. Although a scan along an arc was illustrated in FIG. 3A, it will be understood by those skilled in the arts that by using two scanning lenses 301, 310 in series, suitably oriented at an angle with respect to one another, and suitably positioned with respect to the incident beam 302, as shown in FIG. 3C, a two-dimensional scan pattern can optionally be produced by the scattered beam 303 at the target 305. As illustrated, scattered beam 303 is incident upon target region 304, but other target regions can be illuminated by suitably rotating the lens 310 with the lens rotator 308, and/or moving the target 305 with the target mover 309. Alternatively, it will be understood by those skilled in the arts, that by using multiple lenses oriented at specific angles with respect to the beam, and suitably moving one or another into the beam, different incident angles and therefore different energies may be selected for the system.

The motion of the crystal may be achieved by a variety of mechanical methods, or alternatively by other methods, for examples, piezoelectric, thermal, or sonic methods.

In order to scan a target with a cross-sectional area, the target 305 may be moved as the crystal is rotated, for example by using target mover 309, so that the arc of the circle over which the beam is deflected is swept over the surface of the target. In addition, other arcs may be scanned across the target by suitable choice of other order reflection maxima (different values of n). Motion of the target can be stopped and the lens positioned so as to pay further attention to an area where scanning results indicate further investigation is appropriate.

Rather than using Bragg refraction from a crystal surface, as illustrated in FIG. 3A, a Laue lens may be used for the same purpose, as shown in FIG. 3B. In this configuration the specific direction of the scattered beam 313 is determined by the crystal spacing and the angle of lens 311 that deflects the incident beam 312. (The incident angle should be chosen to represent a maximum of Laue diffraction for the chosen crystal spacing and orientation and the desired photon energy.)

Mechanical motion of the lens 311 may be provided and controlled for positioning the lens 311 in continuous or stepwise motion. The motion may be rotary motion about an axis 316 to produce a range of possible lens positions shown for example as lens 311 and lens 311a. The lens may be rotated by a lens rotator 318. In particular, if the rotation is about an axis 316 that is along the incident beam direction 312, then as the crystal is rotated the incident angle will be constant, and Bragg scattering will continue at the maximum. Thus, depending on the controlled angular position of the lens 311 the scattered beam may follow the path indicated by scattered beam 313a or the path indicated by scattered beam 313, and/or may be scanned along a path between that of scattered beam 313 and scattered beam 313a and may be incident on target 315 at target region 314a or target region 314 (or at regions of the target 315 between target region 314 and target region 314a). (FIG. 3A only shows the beam deflection as a projection in the plane of the diagram, but there is also a component of deflection out of the diagram plane as the crystal lens 311, 311a rotates. See also the discussion hereinbelow of FIG. 4.)

A series of lenses may be used. Although a scan along an arc is illustrated in FIG. 3B, it will be understood by those skilled in the arts that by using two scanning lenses in series, suitably oriented at an angle with respect to one another, and suitably positioned, a two-dimensional scan pattern can optionally be produced at the target 315. Alternatively, it will be understood by those skilled in the arts, that by using multiple lenses oriented at specific angles with respect to the beam, and suitably moving one or another into the beam, different incident angles and therefore different energies may be selected for the system.

The motion of the crystal may be achieved by a variety of mechanical methods, or alternatively by other methods, for examples, piezoelectric, thermal, or sonic methods.

In order to scan a target with a cross-sectional area, the target 315 may be moved as the crystal is rotated, for example by using target mover 319, so that the arc of the circle over which the beam is deflected is swept over the surface of the target. In addition, other arcs may be scanned across the target by suitable choice of other order reflection maxima (different values of n). Motion of the target can be stopped and the lens positioned so as to pay further attention to an area where scanning results indicate further investigation is appropriate.

Another illustration of a similar embodiment for scanning a photon beam is shown in FIG. 4. The diffracting crystal 402 is rotated about an axis 403 that is coincident with the photon beam 401, maintaining the orientation of the beam and its crystalline planes at the same angle. The scattered beam 404 follows a conical scanning pattern around the beam axis and traces out a cone that projects on the container target being scanned as a circle 405 (or an arc thereof, depending on the container size) in the case of a container whose face is perpendicular to the incident beam axis. The dimensions of the scanned line on the target face depend on the angle of the deflected beam and the distance to the object scanned. This dependence is given by standard geometrical considerations. For clarity, the path 405 of the scattered beam 404 is shown rotated from its actual configuration in FIG. 4. For example, it will be understood that if the crystal 402 is rotated about an axis parallel to and coincident with the incident beam 401, the path 405 will (if the target has a face perpendicular to the incident beam 401) trace out a circle in a plane perpendicular to the incident beam.

Although Laue diffraction is illustrated in FIG. 4, it will be understood that Bragg diffraction also may be used in suitable geometries.

X-Ray Energy Filtering

An application of crystal diffraction using a Laue lens is the energy filtering of an X-ray beam. For example, a Laue crystal can be used to select and focus an energy region (or multiple energy regions) from a continuous X-ray beam produced by electron bremsstrahlung or other methods that produce a beam with a broad energy spectrum. This can both reduce the background from interactions of photons in the beam that do not contribute to the "signal" and reduce the dose delivered to the inspection volume. In this case, the Laue lens acts as a narrow-band energy filter. This principle can also be used to create high or low pass filters, which filter photons above or below an energy threshold.

The use of a bremstrahlung photon beam, or other photon beam produced by a method that provides a broad energy spectrum, for interrogation of cargo has the possible disadvantage of having photons in an energy range that are not of interest. These photons do not contribute to the signal that is being measured, and may deposit unnecessary dose to the container that is being scanned. Similarly, radiation scattered from a target may have energy regions that are not utilized in the inspection technique.

A Laue lens, which scatters photons of different energies through different angles, can be used as a filter for the broad spectrum of photons. The process can also be used to make a set of diverging photons more collimated.

In FIGS. 5A, 5B and 5C a multi energy photon beam 501, 506, 520 is incident on a Laue lens 502, 507, 522. For clarity the lens is shown rotated from its actual orientation in FIGS. 5A, 5B and 5C. (For example, as deployed the beams 501 and 520 in FIGS. 5A and 5C are incident on the plane containing the crystal surfaces arranged in concentric circles, such that the central axis of the beam is substantially perpendicular to the plane containing the crystal lens. In FIG. 5B, the beam 506 is incident on the plane containing the crystal surfaces arranged in rows, such that the plane of the beam is substantially perpendicular to the plane containing the lens.)

Depending on the desired energy range, and the crystal chosen, each crystal surface in a given concentric circle (or, for FIG. 5B, in a given row) may be oriented at an appropriate angle such that photons of the desired energy range are incident on each crystal surface at a desired angle and are deflected in the desired direction. The lens deflects lower energy photons 503, 508, 524 more strongly than higher energy photons 504, 510, 526.

In FIG. 5A, cylindrical symmetry is shown and the low energy photons 503 are focused to the center of the beam where they are absorbed (for example, by a high-Z material such as lead) in absorber 505. In FIG. 5B, a planar or fan beam 506 is passed through a Laue lens 507, which deflects the low energy photons 508 so that they are absorbed by absorber 509 while higher energy photons 510 are passed. In FIG. 5C, a cylindrical symmetry is shown again. The lower energy photons 524 are focused to the center of the beam where they are absorbed by absorber 530. The higher energy photons 526 are least focused and are absorbed by high energy absorber 532. The intermediate energy photons 528 are focused an intermediate amount by the lens 522 and are passed, forming a band pass filter for selecting photons having a selected range of energies. In the system of FIG. 5C, by optionally omitting the absorber 530, a low pass filter is formed for selecting photons having an energy lower than a selected energy.

Although the configuration in FIG. 5C shows cylindrical symmetry, it will be apparent to those skilled in the art that corresponding band pass and low pass filters can be formed for the planar or fan beam configuration of FIG. 5B by suitable placement of absorbers.

The configurations shown in FIGS. 5A and 5C, in addition to performing energy filtering, also are capable of forming a filtered and collimated beam of high energy photons 504 (FIG. 5A) or selected intermediate energy photons 528 (FIG. 5C) as shown. In all of the configurations shown in FIGS. 5A, 5B and 5C, only photons in the desired energy range are passed through the lens/absorber system.

The invention claimed is:

1. A method for illuminating a target to analyze its contents, comprising:
   a) providing a source of photons in an X-ray energy range including photons of energy greater than 100 keV;
   b) locating a crystal lens comprised of a plurality of lens surfaces arranged in at least one concentric circle, at a predetermined location relative to the photon source such that a beam of photons from the photon source is incident on said plurality of lens surfaces at at least one preselected angle of incidence to the surfaces; and
   c) locating a target at a predetermined location relative to the crystal lens such that a plurality of photons from the photon beam in a preselected energy range are diffracted by the lens surfaces to be incident on a preselected portion of the target;
   further comprising moving the target such that a plurality of the diffracted photons scan at least a portion of a target surface.

2. A method for illuminating a target to analyze its contents, comprising:
   a) providing a source of photons in an X-ray energy range including photons of energy greater than 100 keV;
   b) locating a crystal lens comprised of a plurality of lens surfaces arranged in at least one concentric circle, at a predetermined location relative to the photon source such that a beam of photons from the photon source is incident on said plurality of lens surfaces at at least one preselected angle of incidence to the surfaces; and
   c) locating a target at a predetermined location relative to the crystal lens such that a plurality of photons from the photon beam in a preselected enemy range are diffracted by the lens surfaces to be incident on a preselected portion of the target;
   further comprising rotating the crystal lens about an axis such that a plurality of the diffracted photons in the preselected energy range scan at least a portion of a target surface.

3. A system for illuminating a target to analyze its contents, comprising:
   a) a source of photons in an X-ray energy range including photons of energy greater than 100 keV;
   b) a crystal lens comprised of a plurality of lens surfaces arranged in at least one concentric circle, at a predetermined location relative to the photon source such that a beam of photons from the photon source is incident on said plurality of lens surfaces at at least one preselected angle of incidence to the surfaces; and
   c) a target at a predetermined location relative to the crystal lens such that a plurality of photons from the photon beam in a preselected energy range are diffracted by the lens surfaces to be incident on a preselected portion of the target;
   further comprising means for moving the target such that a plurality of the diffracted photons scan at least a portion of a target surface.

4. A system for illuminating a target to analyze its contents, comprising:
  a) a source of photons in an X-ray energy range including photons of energy greater than 100 keV;
  b) a crystal lens comprised of a plurality of lens surfaces arranged in at least one concentric circle, at a predetermined location relative to the photon source such that a beam of photons from the photon source is incident on said plurality of lens surfaces at at least one preselected angle of incidence to the surfaces; and
  c) a target at a predetermined location relative to the crystal lens such that a plurality of photons from the photon beam in a preselected energy range are diffracted by the lens surfaces to be incident on a preselected portion of the target;
  further comprising means for rotating the crystal lens about an axis such that a plurality of the diffracted photons in the preselected energy range scan at least a portion of a target surface.

5. A method for illuminating a target to analyze its contents, comprising:
  a) providing a source of photons in a preselected X-ray energy range including photons of energy greater than 100 keV;
  b) locating a crystal lens at a predetermined location and orientation relative to the photon source such that a beam of photons from the photon source is incident on said lens at a preselected angle of incidence; and
  c) locating a target at a predetermined location relative to the crystal lens such that a plurality of photons from the photon beam are diffracted by the lens to be incident on a preselected portion of the target;
  further comprising moving the target such that a plurality of the diffracted photons scan at least a portion of a target surface.

6. A method for illuminating a target to analyze its contents, comprising:
  a) providing a source of photons in a preselected X-ray energy range including photons of energy greater than 100 keV;
  b) locating a crystal lens at a predetermined location and orientation relative to the photon source such that a beam of photons from the photon source is incident on said lens at a preselected angle of incidence; and
  c) locating a target at a predetermined location relative to the crystal lens such that a plurality of photons from the photon beam are diffracted by the lens to be incident on a preselected portion of the target;
  further comprising rotating the crystal lens about an axis substantially parallel to the photon beam such that a plurality of the diffracted photons scan at least a portion of a target surface.

7. A system for illuminating a target to analyze its contents, comprising:
  a) a source of photons in a preselected X-ray energy range including photons of energy greater than 100 keV;
  b) a crystal lens at a predetermined location and orientation relative to the photon source such that a beam of photons from the photon source is incident on said lens at a preselected angle of incidence; and
  c) a target at a predetermined location relative to the crystal lens such that a plurality of photons from the photon beam are diffracted by the lens to be incident on a preselected portion of the target;
  further comprising means for moving the target such that a plurality of the diffracted photons scan at least a portion of a target surface.

8. A system for illuminating a target to analyze its contents, comprising:
  a) a source of photons in a preselected X-ray energy range including photons of energy greater than 100 keV;
  b) a crystal lens at a predetermined location and orientation relative to the photon source such that a beam of photons from the photon source is incident on said lens at a preselected angle of incidence; and
  c) a target at a predetermined location relative to the crystal lens such that a plurality of photons from the photon beam are diffracted by the lens to be incident on a preselected portion of the target;
  further comprising means for rotating the crystal lens about an axis substantially parallel to the photon beam such that a plurality of the diffracted photons scan at least a portion of a target surface.

9. A method for illuminating a target to analyze its contents, comprising:
  a) providing a source of photons comprising photons at a range of X-ray energies including photons of energy greater than 100 keV;
  b) locating a crystal lens comprised of a plurality of lens surfaces arranged in at least one concentric circle, at a predetermined location relative to the photon source such that a beam of photons from the photon source is incident on said plurality of lens surfaces at at least one preselected angle of incidence to the surfaces;
  c) locating at least one low energy absorber and at least one high energy absorber at predetermined locations relative to the crystal lens such that photons from the photon source below a preselected first energy are diffracted by the lens surfaces to be incident on the at least one low energy absorber, and photons from the photon source above a preselected second energy are diffracted by the lens surfaces to be incident on said at least one high energy absorber; and
  d) locating a target at a predetermined location relative to the crystal lens such that a plurality of photons from the photon beam between the preselected first energy and the preselected second energy are diffracted by the lens surfaces to be incident on a preselected portion of the target.

10. The method of claim 9, wherein the diffraction is Laue diffraction.

11. The method of claim 9, wherein the crystal surfaces are composed of an element chosen from a group consisting of carbon, copper, silicon and germanium.

12. The method of claim 9, wherein the crystal surfaces are composed of an element chosen from a group consisting of silver and gold.

13. A system for illuminating a target to analyze its contents, comprising:
  a) a source of photons comprising photons at a range of X-ray energies including photons of energy greater than 100 keV;
  b) a crystal lens comprised of a plurality of lens surfaces arranged in at least one concentric circle, at a predetermined location relative to the photon source such that a beam of photons from the photon source is incident on said plurality of lens surfaces at at least one preselected angle of incidence to the surfaces;
  c) at least one low energy absorber and at least one high energy absorber at predetermined locations relative to the crystal lens such that photons from the photon source below a preselected first energy are diffracted by the lens surfaces to be incident on the at least one low energy absorber, and photons from the photon source above a preselected second energy are diffracted by the lens surfaces to be incident on said at least one high energy absorber; and d) a target at a predetermined location relative to the crystal lens such that a plurality of photons from the photon beam between the preselected first energy and the preselected second energy are diffracted by the lens surfaces to be incident on a preselected portion of the target.

14. The system of claim 13, wherein the diffraction is Laue diffraction.

15. The system of claim 13, wherein the crystal surfaces are composed of an element chosen from a group consisting of carbon, copper, silicon and germanium.

16. The method of claim 13, wherein the crystal surfaces are composed of an element chosen from a group consisting of silver and gold.

17. A method for illuminating a target to analyze its contents, comprising:

a) providing a source of photons in a preselected X-ray energy range including photons of energy greater than 100 keV;

b) locating a first crystal lens at a predetermined location and orientation relative to the photon source such that a beam of photons from the photon source is incident on said first lens at a first preselected angle of incidence;

c) locating a second crystal lens at a predetermined location and orientation relative to the first lens such that a plurality of photons from the photon beam are diffracted from the first lens to be incident on said second lens at a second preselected angle of incidence; and d) locating a target at a predetermined location relative to the second lens such that a plurality of photons from the photon beam diffracted by the first lens are diffracted by the second lens to be incident on a preselected portion of the target.

18. The method of claim 17, wherein the diffraction is Laue diffraction.

19. The method of claim 17, wherein the diffraction is Bragg diffraction.

20. The method of claim 17, wherein the crystal lens is composed of an element chosen from a group consisting of carbon, copper, silicon and germanium.

21. The method of claim 17, wherein the crystal lens is composed of an element chosen from a group consisting of silver and gold.

22. A system for illuminating a target to analyze its contents, comprising:

a) a source of photons in a preselected X-ray energy range including photons of energy greater than 100 keV;

b) a first crystal lens at a predetermined location and orientation relative to the photon source such that a beam of photons from the photon source is incident on said first lens at a first preselected angle of incidence;

c) a second crystal lens at a predetermined location and orientation relative to the first lens such that a plurality of photons from the photon beam are diffracted from the first lens to be incident on said second lens at a second preselected angle of incidence; and d) a target at a predetermined location relative to the second lens such that a plurality of photons from the photon beam diffracted by the first lens are diffracted by the second lens to be incident on a preselected portion of the target.

23. The system of claim 22, wherein the diffraction is Laue diffraction.

24. The system of claim 22, wherein the diffraction is Bragg diffraction.

25. The system of claim 22, wherein the crystal lens is composed of an element chosen from a group consisting of carbon, copper, silicon and germanium.

26. The method of claim 22, wherein the crystal lens is composed of an element chosen from a group consisting of silver and gold.

* * * * *